(12) United States Patent
Sznba

(10) Patent No.: US 7,239,724 B2
(45) Date of Patent: Jul. 3, 2007

(54) SECURITY IDENTIFICATION SYSTEM AND METHOD

(75) Inventor: Joseph Sznba, Dearborn, MI (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/344,280

(22) Filed: Jan. 31, 2006

(65) Prior Publication Data

US 2006/0133653 A1 Jun. 22, 2006

Related U.S. Application Data

(63) Continuation-in-part of application No. 10/896,724, filed on Jul. 22, 2004, now Pat. No. 7,035,432.

(51) Int. Cl.
*G06K 9/00* (2006.01)
*G06F 7/04* (2006.01)
*G08B 29/00* (2006.01)
*G08B 13/00* (2006.01)
*G08B 21/00* (2006.01)
*G01G 19/36* (2006.01)

(52) U.S. Cl. .................. 382/115; 340/5.2; 340/541; 340/666; 177/25.11

(58) Field of Classification Search ........ 382/115–118; 340/5.2, 5.52, 5.53, 5.81, 5.82, 5.8, 541, 340/573.1, 666, 5.7
See application file for complete search history.

(56) References Cited

U.S. PATENT DOCUMENTS

| | | | | |
|---|---|---|---|---|
| 3,750,158 A | * | 7/1973 | Anastassakis | 43/59 |
| 4,137,567 A | * | 1/1979 | Grube | 702/175 |
| 4,350,166 A | | 9/1982 | Mobarry | |
| 4,586,441 A | * | 5/1986 | Zekich | 109/8 |
| 4,821,118 A | * | 4/1989 | Lafreniere | 348/156 |
| 5,378,860 A | * | 1/1995 | Dingfelder et al. | 177/25.19 |
| 5,653,462 A | | 8/1997 | Breed et al. | |
| 5,694,320 A | | 12/1997 | Breed | |
| 5,748,473 A | | 5/1998 | Breed et al. | |
| 5,822,707 A | | 10/1998 | Breed et al. | |
| 5,829,782 A | | 11/1998 | Breed et al. | |
| 5,835,613 A | | 11/1998 | Breed et al. | |
| 5,845,000 A | | 12/1998 | Breed et al. | |
| 5,848,802 A | | 12/1998 | Breed et al. | |
| 5,901,978 A | | 5/1999 | Breed et al. | |
| 5,943,295 A | | 8/1999 | Varga et al. | |
| 6,038,465 A | * | 3/2000 | Melton, Jr. | 600/407 |
| 6,039,139 A | | 3/2000 | Breed et al. | |
| 6,078,854 A | | 6/2000 | Breed et al. | |

(Continued)

*Primary Examiner*—Andrew W. Johns
*Assistant Examiner*—Anthony Mackowey
(74) *Attorney, Agent, or Firm*—Howard & Howard Attorneys, P.C.

(57) ABSTRACT

An identification system (10) of the present invention is used at airport terminals, bus stations, government buildings, and the like. The identification system (10) includes a controller (26), a pair of spaced stations or checkpoints (12, 14) for generating a first reference and a second reference each containing scanning image and weight of the person (P) passing through the first (12) and second (14) spaced stations. The controller (26) includes a comparative software that determines a correlation between the first and second references to identify at least one discrepancy therebetween. As the discrepancy is identified, a distress signal is send by the controller (26) to the second station (14) to alert about the discrepancy being identified. The invention includes a method of identifying the person (P).

25 Claims, 4 Drawing Sheets

U.S. PATENT DOCUMENTS

| | | | | |
|---|---|---|---|---|
| 6,081,757 | A | 6/2000 | Breed et al. | |
| 6,088,640 | A | 7/2000 | Breed | |
| 6,116,639 | A | 9/2000 | Breed et al. | |
| 6,119,096 | A * | 9/2000 | Mann et al. | 705/5 |
| 6,134,492 | A | 10/2000 | Breed et al. | |
| 6,141,432 | A | 10/2000 | Breed et al. | |
| 6,168,198 | B1 | 1/2001 | Breed et al. | |
| 6,186,537 | B1 | 2/2001 | Breed et al. | |
| 6,205,233 | B1 * | 3/2001 | Morley et al. | 382/103 |
| 6,234,519 | B1 | 5/2001 | Breed | |
| 6,234,520 | B1 | 5/2001 | Breed et al. | |
| 6,242,701 | B1 | 6/2001 | Breed et al. | |
| 6,253,134 | B1 | 6/2001 | Breed et al. | |
| RE37,260 | E | 7/2001 | Varga et al. | |
| 6,270,116 | B1 | 8/2001 | Breed et al. | |
| 6,279,946 | B1 | 8/2001 | Johnson et al. | |
| 6,283,503 | B1 | 9/2001 | Breed et al. | |
| 6,324,453 | B1 | 11/2001 | Breed et al. | |
| 6,325,414 | B2 | 12/2001 | Breed et al. | |
| 6,330,501 | B1 | 12/2001 | Breed et al. | |
| 6,331,014 | B1 | 12/2001 | Breed | |
| 6,352,517 | B1 | 3/2002 | Flock et al. | |
| 6,393,133 | B1 | 5/2002 | Breed et al. | |
| 6,397,136 | B1 | 5/2002 | Breed et al. | |
| 6,412,813 | B1 | 7/2002 | Breed et al. | |
| 6,422,595 | B1 | 7/2002 | Breed et al. | |
| 6,442,465 | B2 | 8/2002 | Breed et al. | |
| 6,442,504 | B1 | 8/2002 | Breed et al. | |
| 6,445,988 | B1 | 9/2002 | Breed et al. | |
| 6,452,870 | B1 | 9/2002 | Breed et al. | |
| 6,492,634 | B2 | 12/2002 | Marchitto et al. | |
| 6,553,296 | B2 | 4/2003 | Breed et al. | |
| 6,611,195 | B1 * | 8/2003 | Manneschi et al. | 340/5.52 |
| 6,617,970 | B2 * | 9/2003 | Makiyama et al. | 340/573.1 |
| 7,019,644 | B2 * | 3/2006 | Barrie | 340/539.13 |
| 7,051,924 | B2 * | 5/2006 | Nakano et al. | 235/375 |
| 2002/0113715 | A1 * | 8/2002 | Wilson | 340/815.45 |
| 2002/0139853 | A1 * | 10/2002 | Tsikos et al. | 235/462.01 |
| 2002/0154012 | A1 * | 10/2002 | Risi | 340/541 |
| 2002/0167403 | A1 * | 11/2002 | Colmenarez et al. | 340/541 |
| 2002/0173696 | A1 | 11/2002 | Kolarovic et al. | |
| 2002/0191817 | A1 * | 12/2002 | Sato et al. | 382/118 |
| 2003/0020607 | A1 * | 1/2003 | Risi | 340/540 |
| 2003/0133597 | A1 * | 7/2003 | Moore et al. | 382/115 |
| 2003/0190076 | A1 | 10/2003 | DeLean | |
| 2004/0005088 | A1 | 1/2004 | Jeung et al. | |
| 2004/0161133 | A1 * | 8/2004 | Elazar et al. | 382/115 |
| 2004/0190757 | A1 * | 9/2004 | Murphy et al. | 382/115 |
| 2004/0234108 | A1 * | 11/2004 | Li et al. | 382/116 |
| 2005/0002561 | A1 * | 1/2005 | Monachino et al. | 382/159 |
| 2005/0006152 | A1 * | 1/2005 | Eldeiry | 177/25.11 |
| 2005/0083171 | A1 * | 4/2005 | Hamilton | 340/5.7 |
| 2005/0232459 | A1 * | 10/2005 | Rowe et al. | 382/100 |
| 2005/0248450 | A1 * | 11/2005 | Zanovitch | 340/506 |
| 2006/0104480 | A1 * | 5/2006 | Fleisher | 382/103 |
| 2006/0126906 | A1 * | 6/2006 | Sato et al. | 382/118 |

* cited by examiner

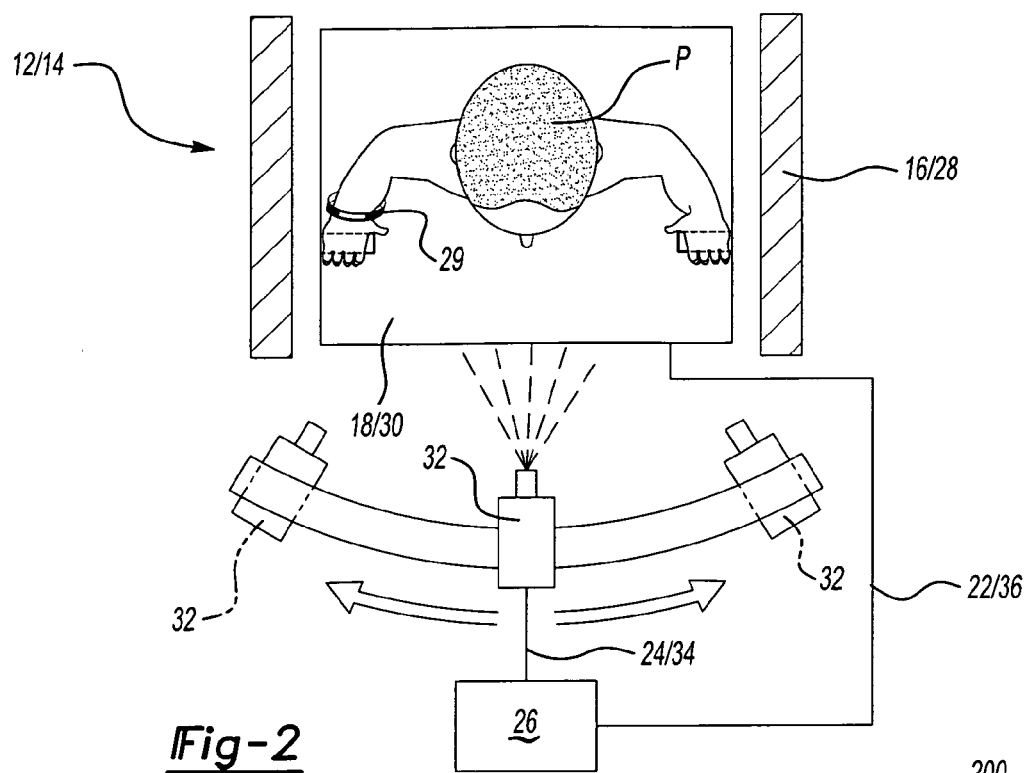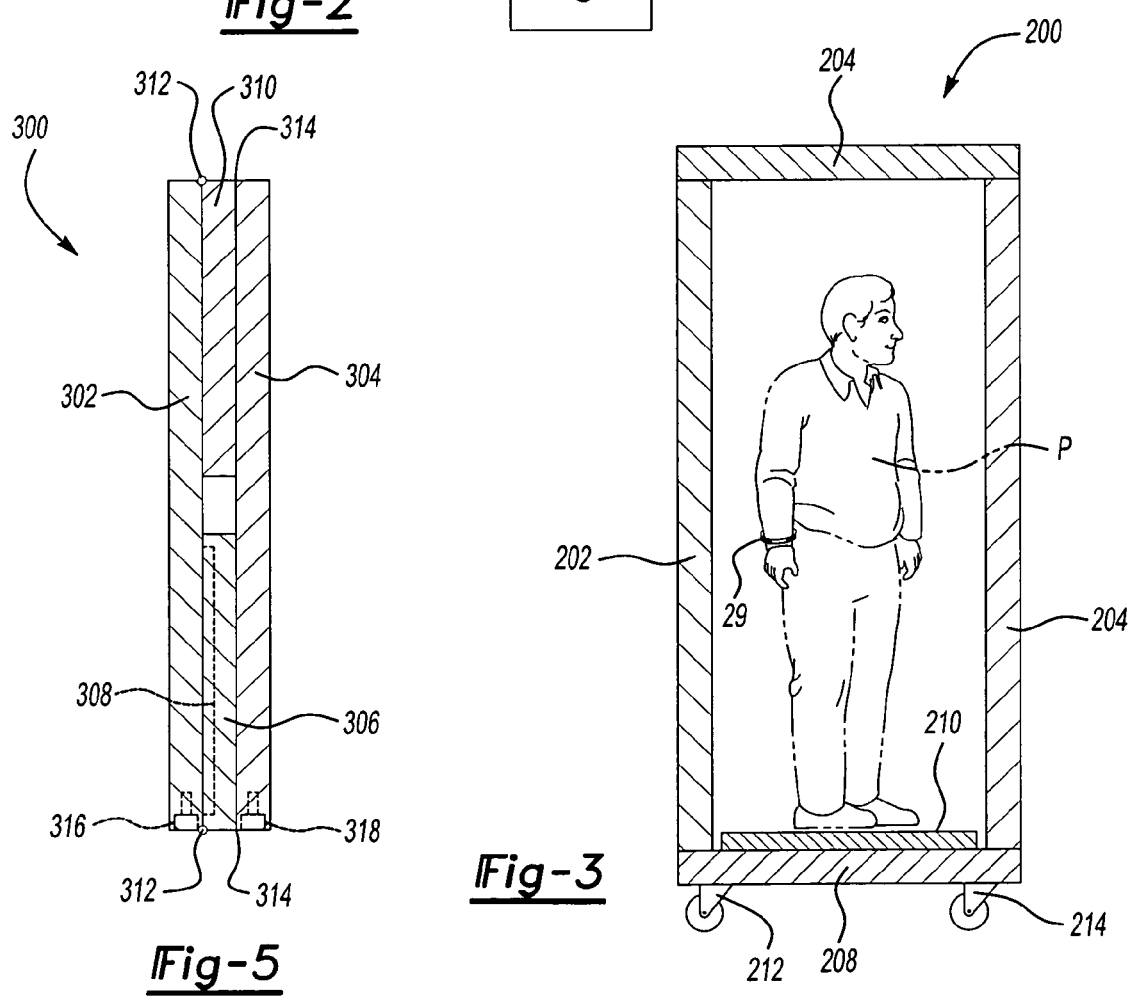

SECURITY IDENTIFICATION SYSTEM AND METHOD

CROSS REFERENCE TO RELATED APPLICATION

This application is a continuation in part application of U.S. patent application Ser. No. 10/896,724 filed Jul. 22, 2004 now U.S. Pat. No. 7,035,432.

BACKGROUND OF THE INVENTION

1. Field of the Invention

This invention relates generally to a security and identification method and system for use in screening and/or identifying individuals passing through secure entry or checkpoints at airport passenger terminals, government offices, office buildings, military facilities, laboratories, and the like.

2. Description of the Prior Art

Passenger and carry-on luggage screening technology was first instituted in 1973 and is still in use today and was originally intended to uncover hijack weapons. Recent national and international events have underscored the need for effective identification and screening of individuals entering or passing through secure checkpoints. Today, the procedure of screening passengers at common carrier terminals, such as, for example, airports, trains stations, bus terminals and the like, must be an important task to protect safety of passengers. Manual identification of the passengers at the checkpoint is a slow and cumbersome process, and because it is not precise, manual identification may allow unwanted or undesirable individuals to avoid detection through disguises.

The art is replete with various systems of facial recognition and identification methods. The U.S. Pat. No. 3,805,238, for example, teaches a primitive method for identifying individuals using selected characteristic body curves; U.S. Pat. No. 4,858,000, teaches an image recognition system designed for use in recognizing predetermined individuals out of a viewing audience; the U.S. Pat. No. 5,163,094 on the other hand teaches a method for identifying individuals by the analysis of elemental shapes derived from biosensor data, generating a thermal image of the individual's face that is converted to a digital representation.

With advent of a modern technology other methods have been developed. The U.S. Pat. No. 5,905,807, teaches an apparatus for processing a facial image and creating an output of extracted data of feature points that may be used for comparison or other purposes; the U.S. Pat. No. 6,111,517, describes a continuous video monitoring system for regulating access to a restricted environment such as a computer system; and the U.S. Pat. No. 6,292,575, teaches a real-time facial recognition and verification system for comparison to a stored image. Other attempts have been made to improve the security identification system.

The United States Publication No. 20030142853, for example, teaches a security and identification system designed to obtain improved images for use by real-time facial recognition and identification systems for screening individuals passing through secure entry or checkpoints such as airport passenger terminals, government offices, and other secure locations. The system detects the presence of a person at the checkpoint, interactively instructs the person to stop and move into position for proper identification and recognition, analyzes the facial features of the subject as the person through the checkpoint, and compares the features of the subject with those in a database. The system then generates different signals depending upon whether or not the person is recognized.

Each of the aforementioned United States patent references describes either a method or apparatus for performing facial recognition or identification. However, all of these patents suffer from the drawback that unless the facial image is properly positioned and lighted for a sufficient length of time, the recognition or identification may be incomplete, inaccurate or may not take place at all. Furthermore, these references do not provide a way to account for a passenger's whereabouts after the passenger has gone through the security checkpoint up to and when the passenger boards the transportation vehicle.

SUMMARY OF THE INVENTION

An identification system of the present invention is designed for screening and/or identifying individuals passing through a secure entry or checkpoints such as airport passenger terminals, government offices, office buildings, military facilities, laboratories, and other secure locations. The identification system includes a controller, a first station or checkpoint adaptable for generating a first plurality of pixels and measuring a first weight of the passenger or visitor. The first station signals the controller a location of the first plurality of pixels and value of the first weight thereby generating a first reference as the passenger or the visitor passed through the first station.

A second station or checkpoint is spaced from the first station. Similarly to the first station, the second station generates a second plurality of pixels and a second weight of the passenger or the visitor thereby signaling the controller a location of the second plurality of pixels and value of the second weight of the passenger or the visitor thereby generating a second reference as the passenger or the visitor passes through the second station. The controller includes a comparative software which integrates the first reference and the second reference thereby comparing the first plurality of pixels and the first weight of the first reference with the second plurality of pixels and the second weight of the second reference as the passenger or the visitor passes through the second station. The comparative software determines a correlation between the first plurality of pixels to the second plurality of pixels and the first weight to the second weight for identifying at least one discrepancy. As the discrepancy is identified, a signal is sent to the controller that generates a distress signal to alert about the identified discrepancy. The invention also includes a method of identifying the passenger.

Unlike other prior art technologies, an advantage of the present invention is to provide a security system adaptable to identify a discrepancy between a visual image of the passenger and a weight of the passenger as he or she passes through at least two checkpoints of the security system.

Another advantage of the present invention is to provide a security system and a method adaptable to identify a discrepancy between the weight of the passenger even if the visual image determined by the security system at the at least two checkpoints is identical.

BRIEF DESCRIPTION OF THE DRAWINGS

Other advantages of the present invention will be readily appreciated as the same becomes better understood by reference to the following detailed description when considered in connection with the accompanying drawings wherein:

FIG. 2 shows a cross sectional and a partially schematic view of a checkpoint of the inventive security system that illustrate an alternative embodiment of a camera movable relative a passenger to electively develop 2 or 3 dimensional image of the passenger;

FIGS. 3 and 4 shows a first alternative embodiment of the checkpoint defined by a kiosk having wheels to be transportable and movable between various locations, such as, for example, gates at the airport terminal, and the like;

FIG. 5 shows a second alternative embodiment of the checkpoint defined by the kiosk being collapsible to be transported between different airport terminals, and the like.

DETAILED DESCRIPTION OF THE PREFERRED EMBODIMENT

Figure 1:
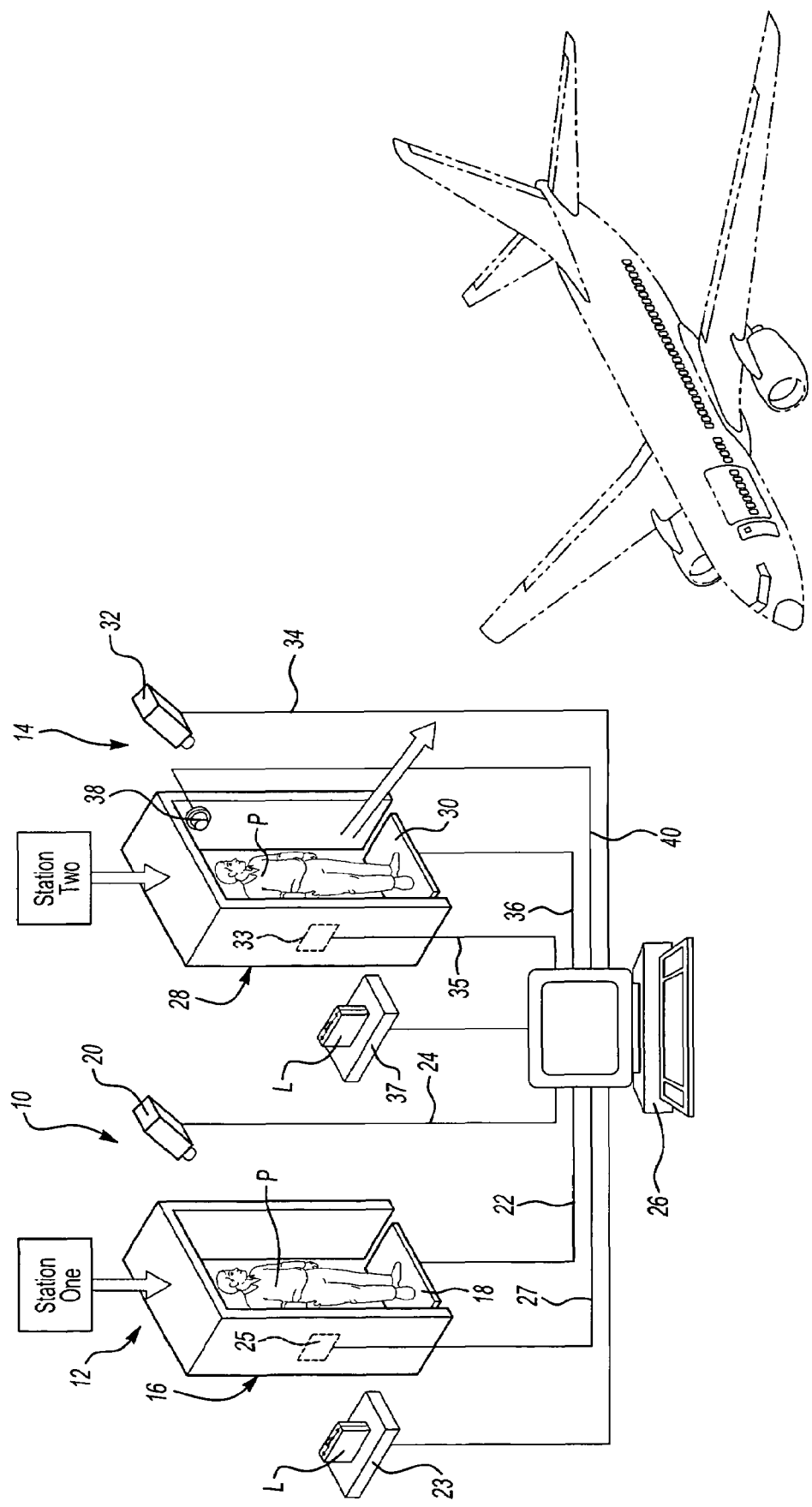
FIG. 1 shows a front and a partially schematic illustration of an inventive security system.

Referring to FIG. 1, a preferred embodiment of the present security identification system (the system) is generally shown at 10. The system 10 is designed for screening and/or identifying individuals passing through a secure entry or checkpoints such as airport passenger terminals, government offices, office buildings, military facilities, laboratories, and other secure locations.

As illustrated in FIG. 1, the system 10 includes a pair of spaced stations or checkpoints, generally shown at 12 and 14, respectively. The first station 12 is used as initial screening point at the airport or the government building. The first checkpoint 12 includes a gate, generally indicated at 16, and a weight measuring device 18, such as, for example a scale, as known to those skilled in the art. The weight measuring device 18 electronically communicates 22 with a processor or a controller 26.

A vision system or a camera 20 is placed above the person P as the person P passes through the gate 16 and contacts the weight measuring device 18 thereby activating the camera 20. The camera 20 is provided to scan the person P to generate a 2-dementional or the 3-dimentional image of the person P with or without the luggage L. The camera 20 is preferably mounted to a wall, but may optionally be mounted to the gate, as best shown in FIG. 2. More than one camera 20 is alternatively used to further enhance the image of the person P. As will be discussed further below, the camera 20 generates sequential images of the person P with or without the luggage L and transmits those images and weights to the controller 26. In one embodiment, the carry-on luggage is weighed on a separate luggage scale 23. The camera 20 is preferably hard wired 24 to the controller 20. However, in an alternate embodiment, the camera includes an RF or equivalent transmitter and signals a remote processor (not shown) with the image of the person P being generated. The gate 16 includes a detection device 25 disposed inside the wall of the gate 16. The detection device 25 is electronically communicated 27 with the controller 26. The detection device 25 is adaptable for detecting any metal objects (not shown) carried by the person P. The detection device 25 is also adaptable for scanning an identification number printed on a wrist cuff of bracelet 29 issued to the person P at E-checkpoint at the airport and carried by the person P on the person's P wrist. In one preferred embodiment, hand supports 31 are included to locate the bracelet in a position desirable for investigation and scanning.

Technological advances and cameras, such as, the camera 20 have produced high resolution images capable of generating a significant number of pixels from a received image. By transmitting the image to the controller 26, the camera 20 enables the controller 26 to record and detect through a comparative software generating computer algorithms minor changes in sequential images transmitted by the camera 20. The camera 20 is capable of generating the high resolution images that provide a high number of pixels. The camera 20 includes several alternatives, such as, for example charge coupled cameras, high dynamic range cameras, active pixel cameras, and complementary metal oxides semi-conductor cameras and their equivalents. Each of these cameras provide the high resolution necessary to generate the plurality of pixels required for the controller 26 to measure variations in pixels between sequentially generated images. It may be necessary to provide an infrared transmitter (not shown) to enhance the image of the person P generated by the camera 20. The infrared transmitter is particularly relevant when a satisfactory amount of light is not available such as, for example, during night time. Alternatively, the camera 20 capable of detecting electromagnetic radiation also produces sufficient resolution.

As the person P passes through the gate 16, the camera 20 scans the person P to generate a first plurality of pixels that include contour of the person P, facial characteristics, and the like. The location of the first plurality of pixels is transmitted and stored in the controller 26. While the camera 20 generates the first plurality of pixels, the measuring device 18 weights the person P and transmits the weight taken, such as a first value of the weight of the person P to the controller 26. The controller 26 integrated the location of the first plurality of pixels and the first value of the weight to generate a first reference as the person P passed through the first station 12.

As shown in FIG. 1, the second station 14 includes a second gate, generally indicated at 28. A second camera 32 is placed above the person P as the person passes through the second gate 28 just prior to boarding a plane (shown in phantom) or other secured means of transportation. The second station 14 includes a second weight measuring device 30 and a second luggage scale 37 electronically communicating 36 with the controller 26. Similarly to the design of the first station 12, the camera 32 of the second station 14 is provided to scan the person P to generate a 2-dimensional or the 3-dimensional image of the person P. The camera 32 is preferably mounted to the wall (not shown), but may optionally be mounted to the second gate 28, as best shown in FIG. 2. The camera 32 is preferably hard wired 34 to the controller 26. However, as discussed above, in an alternate embodiment, the camera 32 includes an RF or equivalent transmitter and signals a remote processor (not shown) with the image of the person P being generated.

The second gate 28 includes a second detection device 33 disposed inside the wall of the second gate 28. The detection device 33 electronically communicates 35 with the controller 26. The detection device 33 is adaptable for detecting any metal objects (not shown) carried by the person P. The detection device 33 is also adaptable for scanning an identification number printed on the wrist cuff of the bracelet 29 issued to the person P at E-checkpoint at the airport and carried by the person P on the person's P wrist as the person P passes through the second gate 28. An alarm or signaling device 38 electronically communicates 40 with the controller 26. The alarm device 38 includes several alternatives such as, for example, an optical device, a sound transmitting device, and the like. The function of the alarm device 38 will be discussed as the description of the present invention proceeds.

Referring again to FIG. 1, as the person P passes through the second gate 28 before boarding the plane, the camera 32 scans the person P to generate a second plurality of pixels that include contour of the person's P, facial characteristics, and the like. The location of the second plurality of pixels is transmitted and stored in the controller 26. As the camera 32 generates the second plurality of pixels, the measuring device 30 weighs the person P and transmits the weight taken, such as a second value of the weight of the person P to the controller 26. The controller 26 integrates the location of the second plurality of pixels and the second value of the weight to generate a second reference as the person P has not passed beyond the second station.

Alluding to the above, the comparative software (not shown) of the controller 26 compares the first plurality of the pixels with the second plurality of the pixels and the first value of the weight with the second value of the weight to determine correlation. The comparative software of the controller 26 also compares reading of an identification number, as printed or embedded in the wrist cuff or the bracelet, taken or screened by the respective detection devices 25 and 33. As the discrepancy is identified by the comparative software, which may be the discrepancy between the first value of the weight and the second value of the weight, location of the first plurality of pixels and the second plurality of pixels, or for example, any other combination thereof, or the discrepancy between the identification numbers, the comparative software will generate an alarm signal in response to the discrepancies identified. The alarm signal is transmitted to the controller 26. The controller 26 transmits an electronic signal to the alarm or signaling device 38. The alarm device 38 generates optical signal or an alarming sound to notify the authorities about potential threat and opportunity for further investigations. Alternatively, the location of the second plurality of pixels and the second weight taken at the second station 28 may be stored in the controller 26 for a pre-determined period of time to form a database, if the discrepancies are not identified.

Figure 4:
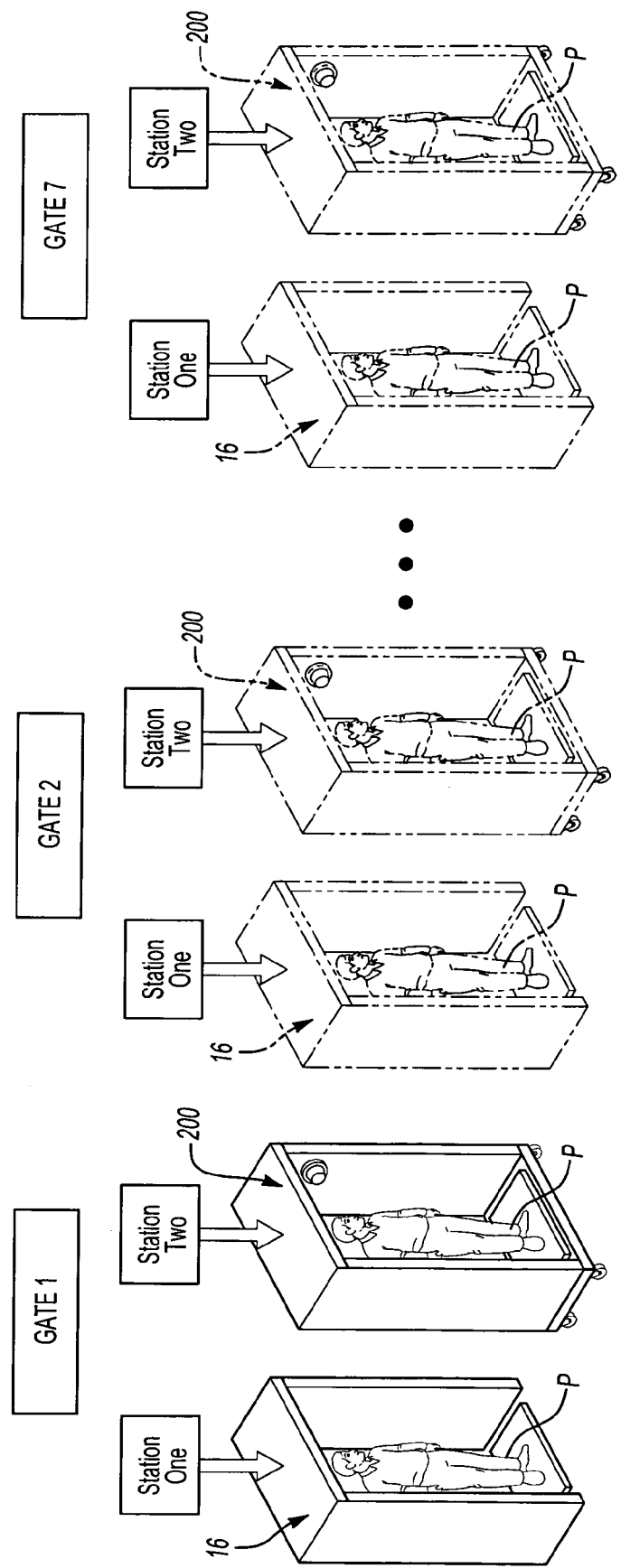
Figure 6:
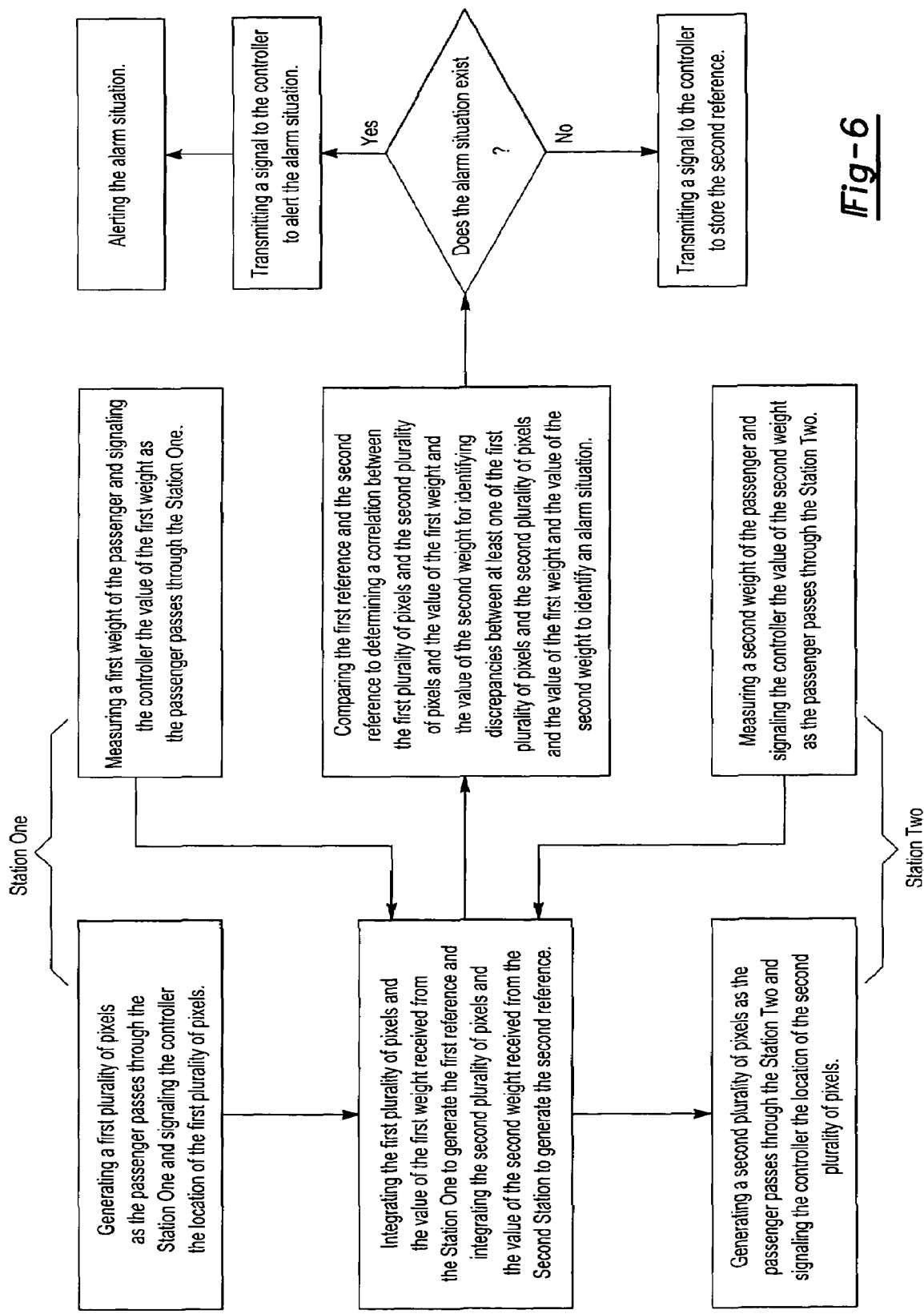
FIG. 6 shows a flow diagram of the logic pattern used by the inventive method.

Referring to FIGS. 3 and 4, the second gate 28 includes several alternative embodiments, generally shown at 200 and 300, respectively. As illustrated in FIG. 3, the second gate 200 includes side walls 202 and 204 interconnected by a top wall 204 and a bottom wall 208. The bottom wall 208 supports a weight measuring device 210. A pair of spaced wheel assemblies 212 and 214 is attached to the bottom wall 208 to move the second gate 200 between several remote locations such as, departing gates at the airports, as shown in phantom in FIG. 4. The wheel assemblies 212 and 214 are rigidly connected to the bottom wall 208 and include brakes (not shown), respectively, to prevent movement of the second gate 200 when the second gate 200 is used to identify the person P. Alternatively, the wheel assemblies 212 and 214 may be foldable into the bottom wall 208 as the second gate 200 is used to identify the person P and retractable from the bottom floor 208 as the second gate 200 is moved between or to remote locations. The mechanical aspects of the wheel assemblies 212 and 214, being foldable or as held in place by the brakes, are known to those skilled in the art.

FIG. 5 illustrates the second alternative embodiment of the second gate 300. The second gate 300 presents side walls 302 and 304, a bottom wall 306 having a weight measuring device 308 installed therein, and a top wall 310. The top wall 310 and the bottom wall 306 are hinged 312 to the side wall 302 and are mechanically interconnected 314 with the side wall 304. To move the second gate 300 to the remote location such as, for example, another airport, or simply to store the second gate 300, the side wall 304 is disengaged from the top wall 310 and the bottom wall 306. The top wall 310 and the bottom wall 306 are collapsed to extend along the side wall 302. The side wall 304 is then placed on top of the bottom wall 306 and the top wall 310 in a sandwich-like fashion. The side walls 302 and 304 are then interconnected by fasteners or an equivalent (not shown). A pair of wheel assemblies 316 and 318 are foldable into or retractable to and from the side walls 302 and 304 of the second gate 300.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

The invention claimed is:

1. An identification system for identifying a person entering a secured area, comprising:
   a controller,
   an identification device generating a first plurality of pixels as the body of the person is scanned in unison with measuring a first weight of the body of the person at a first location and generating a second plurality of pixels as the body of the person is scanned in unison with measuring a second weight of the body of the person at a second location spaced from said first location and signaling said controller a location of said plurality of the pixels and values of the weight taken at said first and second locations for generating a pair of references, and
   a comparator administered by said controller for comparing said pair of references thereby determining a correlation between said plurality of the pixels and said values of the weight taken at said first and second locations for generating a signal in response to discrepancies identified by said comparator between said plurality of the pixels and said values of the weight.

2. The identification system as set forth in claim 1, wherein said identification device is further defined by a first station positioned at said first location and for generating a first plurality of the pixels and measuring a first value of the weight of the person for signaling said controller a location of said first plurality of the pixels said first value of the weight thereby generating one of said references as the person passes through said first station.

3. The identification system as set forth in claim 2, wherein said identification device is further defined by a second station positioned at said second location for generating a second plurality of the pixels and measuring a second value of the weight of the person thereby signaling said controller a location of said second plurality of the pixels and said second value of the weight for generating the other of said references as the person passes through said second station.

4. The identification system as set forth in claim 3, wherein said comparator compares said first plurality of the pixels with said second plurality of the pixels and said first value of the weight with said second value of the weight to determine at least one correlation.

5. The identification system as set forth in claim 2, wherein said first station includes a first camera for scanning the person and a first weight measuring device for measuring weight of the person, said first camera and said first weight measuring device each operatively communicating with said controller.

6. The identification system as set forth in claim 5, wherein said second station includes a second camera for scanning the person and a second weight measuring device for measuring weight of the person, said second camera and said second weight measuring device each operatively communicating with said controller.

7. The identification system as set forth in claim 6, including an alarm device operated by said controller for generating said signal as said discrepancies between said first plurality of the pixels and said second plurality of the pixels or said first value of the weight and said second value of the weight are identified.

8. The identification system as set forth in claim 6, wherein at least one of said first camera and said second camera is a charge-coupled camera.

9. The identification system as set forth in claim 6, wherein at least one of said first camera and said second camera is a high dynamic range camera.

10. The identification system as set forth in claim 6, wherein at least one of said first camera and said second camera is an active pixel camera.

11. The identification system as set forth in claim 6, wherein at least one of said first camera and said second camera is a metal oxide semiconductor camera.

12. An identification system for identifying a person entering a secured area, comprising:
a controller,
a first identification station having a reference imager generating a first three dimensional reference image and a reference weight measuring device generating reference weight of the person entering the secured area each electronically communicating with said controller for signaling said controller said first three dimensional reference image and said reference weight thereby generating a reference data point associated with said first identification station;
a second identification station spaced from said first identification station having a secondary reference imager generating a second image from at least two angles thereby capturing and a secondary weight measuring device generating a secondary weight of the person passing through said secured area each being electronically communicating with said controller for signaling said controller said second image from at least two angles and said secondary weight thereby generating a secondary data point associated with said second identification station, and
said controller indicating an alarm situation if said reference data point is different than said secondary data point as at least one of said first three dimensional image differs from said second image and said reference weight differs from said secondary weight.

13. The identification system as set forth in claim 12, wherein said first identification station includes a first luggage scale for weighing carry on luggage at said first identification station and said second identification includes a second luggage scale for weighing carry on luggage at said second identification station.

14. The identification system as set forth in claim 13, wherein said first and second luggage scales electronically communicate with said controller for transmitting to said controller a reference luggage weight and a secondary luggage weight enabling said controller compare said reference luggage weight to said secondary luggage weight and indicate an alarm situation if said first luggage weight is different than said second luggage weight.

15. The identification system as set forth in claim 12, including a secondary imager for reading a coded bracelet at said first and said second identification stations.

16. The identification system as set forth in claim 12, wherein said controller includes a comparative software adaptable for integrating said reference data point and said secondary reference data point thereby comparing a first plurality of the pixels and said first weight of said reference data point with a second plurality of the pixels and said secondary weight of said secondary reference data point for determining a correlation between said first plurality of the pixels to said second plurality of the pixels and said first weight to said secondary weight thereby identifying at least one discrepancy therebetween for generating a signal as said at least one discrepancy is identified.

17. The identification system as set forth in claim 12, wherein said first station includes a first camera for scanning the person comprising one of a charge coupled camera, a high dynamic camera, and a dynamic range camera.

18. The identification system as set forth in claim 17, wherein said second station includes a second camera for scanning the person comprising one of a charge coupled camera, a high dynamic camera, and a dynamic range camera.

19. The identification system as set forth in claim 12, including an alarm device cooperable with said second station and said controller for generating said alarm signal as said discrepancies are identified.

20. A method of identifying discrepancies between visual image and weight of a person passing through a security system, said method comprising the steps of:
connecting a controller to an identification device of the security system,
generating a first plurality of pixels of the person and signaling the controller a location of the first plurality of pixels as the person passes through the identification device at a first location;
measuring a weight of the person to signal the controller the value of the weight measured as the first plurality of pixels are generated;
generating a second plurality of pixels of the person and signaling the controller a location of the second plurality of pixels as the person passes through the identification device at a second location;
measuring the weight of the person at the second location to signal the controller the value of the weight measured as the second plurality of pixels is generated; and
comparing the first plurality of pixels, the second plurality of pixels and the value of the weight to determine a correlation and generate a signal in response to discrepancies identified by the controller between the first plurality of pixels and the second plurality of pixels or the value of the weight taken at the first and the second locations.

21. The method as set forth in claim 20, wherein the step of generating a fist plurality of pixels is further defined by establishing a first station having a first camera for scanning the person and a first weight measuring device for measuring weight of the person.

22. The method as set forth in claim 21, wherein the step of generation a second plurality of pixels is further defined by establishing a second station spaced from the first station and having a second camera for scanning the person and a second weight measuring device for measuring weight of the person.

23. The method as set forth in claim 22, including the step of connecting an alarm device to the second station and the controller to generate the signal as the discrepancies between the first plurality of pixels and the second plurality of pixels and the weight taken at the first and the second locations.

24. The method as set forth in claim 23, wherein the step of comparing the first plurality of pixels and the second plurality of pixels is further defined by the step of integrating a comparative software to the controller to determine the correlation between the first plurality of pixels and the second plurality of pixels and the value of the weight taken at the first and the second locations to generate the signal in response to the discrepancies.

25. The method as set forth in claim 24, wherein the step of comparing the first plurality of pixels and the second plurality of pixels is further defined by the step of storing the location of the first plurality of pixels and the second plurality of pixels and the value of the weight taken at the first and the second locations to generate the signal in response if the disc repancies are not identified.

* * * * *

UNITED STATES PATENT AND TRADEMARK OFFICE
CERTIFICATE OF CORRECTION

PATENT NO. : 7,239,724 B2 Page 1 of 1
APPLICATION NO. : 11/344280
DATED : July 3, 2007
INVENTOR(S) : Joseph Szuba It is certified that error appears in the above-identified patent and that said Letters Patent is hereby corrected as shown below:

In the Inventor section, please delete "Sznba" and insert --Szuba--.

Column 7, lines 34, 35, please insert --for-- between the words "imager" and "generating."

Column 10, line 11, please delete "disc repancies" and insert --discrepancies--.

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,239,724 B2 Page 1 of 1
APPLICATION NO. : 11/344280
DATED : July 3, 2007
INVENTOR(S) : Joseph Szuba It is certified that error appears in the above-identified patent and that said Letters Patent is hereby corrected as shown below:

On front page the name of Assignee (73) should be changed from "International Business Machines Corporation, Armonk, NY (US)" to --Ronjo LLC, Orion, MI (US)--.

Signed and Sealed this

Twenty-fifth Day of November, 2008

JON W. DUDAS
*Director of the United States Patent and Trademark Office*